United States Patent [19]
Breuer et al.

[11] Patent Number: 5,326,891
[45] Date of Patent: Jul. 5, 1994

[54] HYDROPHOBICIZED DOUBLE LAYER HYDROXIDE COMPOUNDS

[75] Inventors: Wolfgang Breuer, Duesseldorf; Hans-Christian Raths, Monheim, both of Fed. Rep. of Germany

[73] Assignee: Henkel Kommanditgesellschaft auf Aktien, Duesseldorf, Fed. Rep. of Germany

[21] Appl. No.: 50,037

[22] PCT Filed: Oct. 21, 1991

[86] PCT No.: PCT/EP91/01993
§ 371 Date: Apr. 29, 1993
§ 102(e) Date: Apr. 29, 1993

[87] PCT Pub. No.: WO92/07795
PCT Pub. Date: Mar. 5, 1992

[30] Foreign Application Priority Data
Oct. 29, 1990 [DE] Fed. Rep. of Germany ....... 4034305

[51] Int. Cl.$^5$ .......................... C07F 19/00; C07F 5/06; C07F 3/02; C07F 3/06
[52] U.S. Cl. ........................................ 556/28; 556/31; 556/49; 556/61; 556/114; 556/131; 556/149; 534/16
[58] Field of Search ..................... 556/28, 31, 49, 114, 556/131, 149, 61; 534/16

[56] References Cited

U.S. PATENT DOCUMENTS

| | | | |
|---|---|---|---|
| 4,351,814 | 9/1982 | Miyata et al. | 423/306 |
| 4,761,188 | 8/1988 | Miyata | 148/6.2 |

FOREIGN PATENT DOCUMENTS

| | | |
|---|---|---|
| 0082569 | 5/1983 | European Pat. Off. |
| 0095783 | 7/1983 | European Pat. Off. |
| 0085167 | 8/1983 | European Pat. Off. |
| 0091146 | 10/1983 | European Pat. Off. |
| 0092256 | 10/1983 | European Pat. Off. |
| 0142773 | 5/1985 | European Pat. Off. |
| 016937 | 1/1986 | European Pat. Off. |
| 0115083 | 3/1986 | European Pat. Off. |
| 0189899 | 8/1986 | European Pat. Off. |
| 0207811 | 1/1987 | European Pat. Off. |
| 0256872 | 2/1988 | European Pat. Off. |
| 0339426 | 2/1988 | European Pat. Off. |
| 1592126 | 10/1970 | Fed. Rep. of Germany |
| 2061156 | 7/1971 | Fed. Rep. of Germany |
| 3019632 | 2/1984 | Fed. Rep. of Germany |
| 3306822 | 8/1984 | Fed. Rep. of Germany |
| 334693 | 7/1985 | Fed. Rep. of Germany |
| 3731919 | 4/1989 | Fed. Rep. of Germany |
| 3833076 | 4/1989 | Fed. Rep. of Germany |
| 3843713 | 11/1989 | Fed. Rep. of Germany |
| 4010606 | 3/1990 | Fed. Rep. of Germany |

OTHER PUBLICATIONS

Chimia 24, (1970), pp. 99–108.
Chemtech, (1986), pp. 58–63.
Jaocs 63, (1986), pp. 691–695.
Happi, (1986), pp. 52–54 and 123.

Primary Examiner—José G. Dees
Assistant Examiner—Porfirio Nazario
Attorney, Agent, or Firm—Ernest G. Szoke; Wayne C. Jaeschke; Henry E. Millson, Jr.

[57] ABSTRACT

Novel hydrophobicized double-layer hydroxide compounds, processes for their production by reaction of double-layer hydroxides with aliphatic mono- and/or dicarboxylic acids, and their uses as alkoxylation catalysts for compounds containing active H atoms or for fatty acid esters.

The hydrophobicized double-layer hydroxide compounds correspond to formula (I)

$$(M(II)_{1-x}M(III)_x(OH)_2)A_a B_b \cdot z H_2O \qquad (I)$$

in which
M(II) is a divalent metal cation selected from the group consisting of magnesium, zinc, calcium, iron, cobalt, copper, cadmium, nickel and manganese;
M(III) is a trivalent metal cation selected from the group consisting of aluminum, iron, chromium, manganese, bismuth and cerium;
A is an equivalent of a monoanion of an aliphatic $C_{2-34}$ monocarboxylic acid or an equivalent of a dianion of an aliphatic $C_{4-44}$ dicarboxylic acid;
B is an anion selected from the group consisting of carbonate, hydrogen carbonate, sulfate, nitrate, nitrite, phosphate, hydroxide, and halide; and
wherein
$0.1 \leq x \leq 0.5$
$0 < a \leq 0.5$
$0 \leq b \leq 0.5$
$0 < a+b \leq 0.5$
$0 \leq z \leq 10$;

but excluding compounds containing the combinations of magnesium and aluminum with carbonate and/or sulfate.

19 Claims, 3 Drawing Sheets

MAGALDRATE, HYDROPHOBICIZED

CHLORIDE-CONTAINING HYDROPHOB. HYDROTALCITE

NITRATE-CONTAINING HYDROTALCITE, HYDROPHOBICIZED

HYDROPHOBICIZED PYROAURITE

HYDROPHOBICIZED DOUBLE LAYER HYDROXIDE COMPOUNDS

FIELD OF THE INVENTION

This invention relates to new hydrophobicized double layer hydroxide compounds, to a process for the production of these compounds by reaction of double-layer hydroxides with aliphatic mono- and/or dicarboxylic acids in an organic solvent or in a kneader and to the use of the hydrophobicized double layer hydroxide layer compounds as alkoxylation catalysts for compounds containing active H atoms or for fatty acid esters.

PRIOR ART

Two-dimensional inorganic polycations with intra-crystalline charge equalization by mobile interlayer anions are also known as "double layer hydroxide compounds" and have been repeatedly described in the literature (Chimia 24, 99 (1970)). Chemically, these compounds are mixed hydroxosalts of 2- and 3-valent metal cations and may be characterized by the following general formula:

$$(M(II)_{1-x}M(III)_x(OH)_2)B * n\ H_2O$$

in which
M(II) is at least one divalent metal ion,
M(III) is at least one trivalent metal ion and
B is an equivalent of a monobasic and/or polybasic inorganic acid
and
x is a number of 0.2 to 0.4 and
n is a number of 0 to 10.

Certain properties of this class of compounds, for example their use as a catalyst material, as ion exchangers and certain medicinal applications, have been summarily described by W. T. Reichle (CHEMTECH, Jan. 1986, 58). Various methods for the production of these compounds on an industrial scale are described in DE-OS 20 61 156.

A well-characterized representative of this class of compounds is hydrotalcite which occurs naturally as a mineral. Synthetic hydrotalcites are also known and are described, for example, in DE-C-15 92 126, DE 33 46 943 A1, DE 33 06 822 A1 and EP 0 207 811 A1. Hydrotalcite is a natural mineral having the following ideal formula:

$$(Mg_6Al_2(OH)_{16})CO_3 * 4\ H_2O$$

of which the structure is derived from that of brucite ($Mg(OH)_2$). Brucite crystallizes in a layer structure with the metal ions in octahedral vacancies between two layers of close-packed hydroxyl ions, only every second layer of the octahedral vacancies being occupied. In hydrotalcite, a few magnesium ions are replaced by aluminium ions so that the layer packet receives a positive charge. This is equalized by the anions which are present in the interlayers together with zeolitic water of crystallization.

The following are mentioned as other typical representatives of this class compounds:

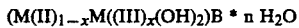

| magaldrate | $(Mg_{10}Al_5(OH)_{31})(SO_4)_2 * n\ H_2O$, |
| pyroaurite | $(Mg_6Fe_2(OH)_{16})CO_3 * 4.5\ H_2O$ and |

-continued

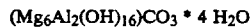

| hydrocalumite | $(Ca_2Al(OH)_6)NO_3 * n\ H_2O$. |

Calcined hydrotalcites have already been used with excellent results as ethoxylation and propoxylation catalysts (DS 38 43 713 A1). However, they are attended by the disadvantage that they have to be converted from the natural and synthetic hydrotalcites into a calcined form suitable for catalytic purposes by heating for several hours at temperatures of, for example, 400° to 600° C. In addition, calcined compounds are sensitive to traces of water and to the carbon dioxide from the air (reverse reaction of calcination), so that their range of applications and their stability in storage are limited due to the loss of activity.

According to DE 30 19 632 A1, U.S. Pat. No. 4,761,188, EP 0 142 773 A1, EP 0 189 899 A1, EP 0 256 872 A1, hydro-phobicized hydrotalcites formed by the treatment of hydrotalcite with anions of acids, for example fatty acids, have already been used as stabilizers for thermoplastic resins. This surface treatment is carried out with anionic surface-active agents in a quantity of 1 to 10% by weight, based on the hydrotalcite.

In addition, it is known from the teaching of DE 37 31 919 A1 that compounds having the general formula $Al_xMg_y(OH)_{35-z}R_z * n\ H_2O$, in which R is the anion of a monocarboxylic acid, may be used as thickeners, thixotropic agents, stabilizers or anti-sedimentation agents. The compounds disclosed in this document are prepared by a complete exchange of sulfate ions for monocarboxylic acid ions using an aqueous suspension of the alkali salt of the monocarboxylic acid.

DE 40 10 606 A1 describes hydrophobicized hydrotalcite compounds having the general formula $Mg_xAl(OH)_y—(CO_3)_m(A)_n * z\ H_2O$, in which A stands for a dianion of an aliphatic dicarboxylic acid or for two monoanions of an aliphatic monocarboxylic acid, as alkoxylation catalysts.

Now, the problem addressed by the present invention was to provide new hydrophobicized double layer hydroxide compounds in which the trivalent aluminium or divalent magnesium would be replaced by equivalent metal cations and the ratio of the anion B to be exchanged to the hydrophobicizing anion A could be varied.

In addition, known double layer hydroxide compounds, which had never been used as alkoxylation catalysts either in pure form or by calcination, were to be converted into an active catalyst form by hydrophobicization.

DESCRIPTION OF THE INVENTION

Figure 1:
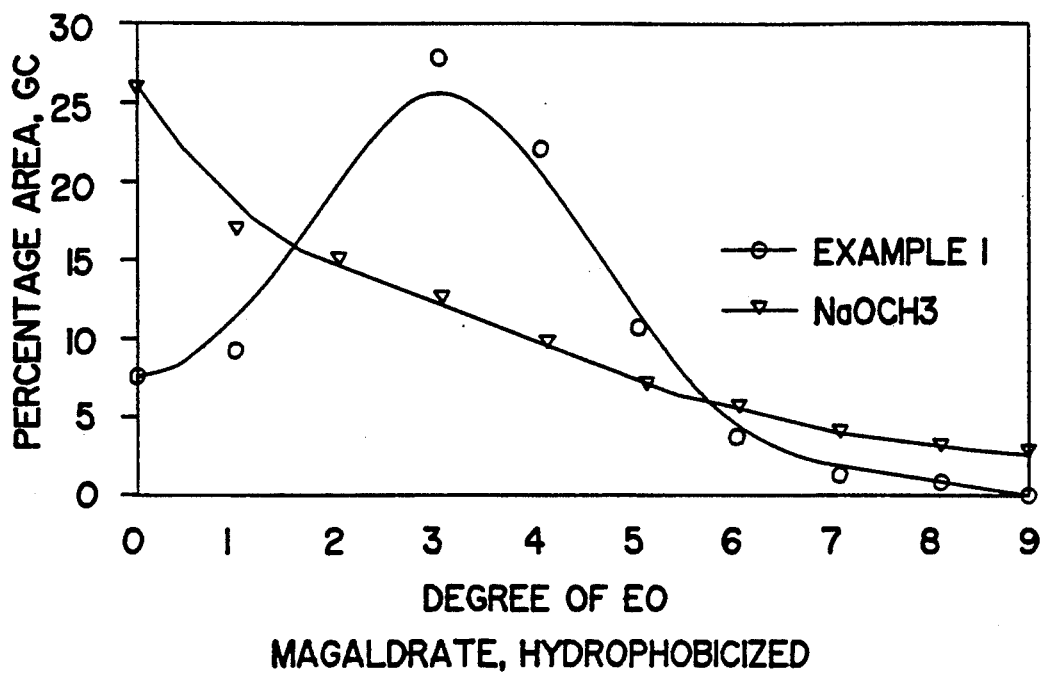
FIGS. 1-6 set forth in graph form the product distributions obtained by GC analysis for the preparation of a fatty alcohol ethoxylate using the catalysts, concentrations, reaction times, and hydroxyl values listed in Table 1, compared to those obtained using $NaOCH_3$ as the catalyst.
Figure 2:
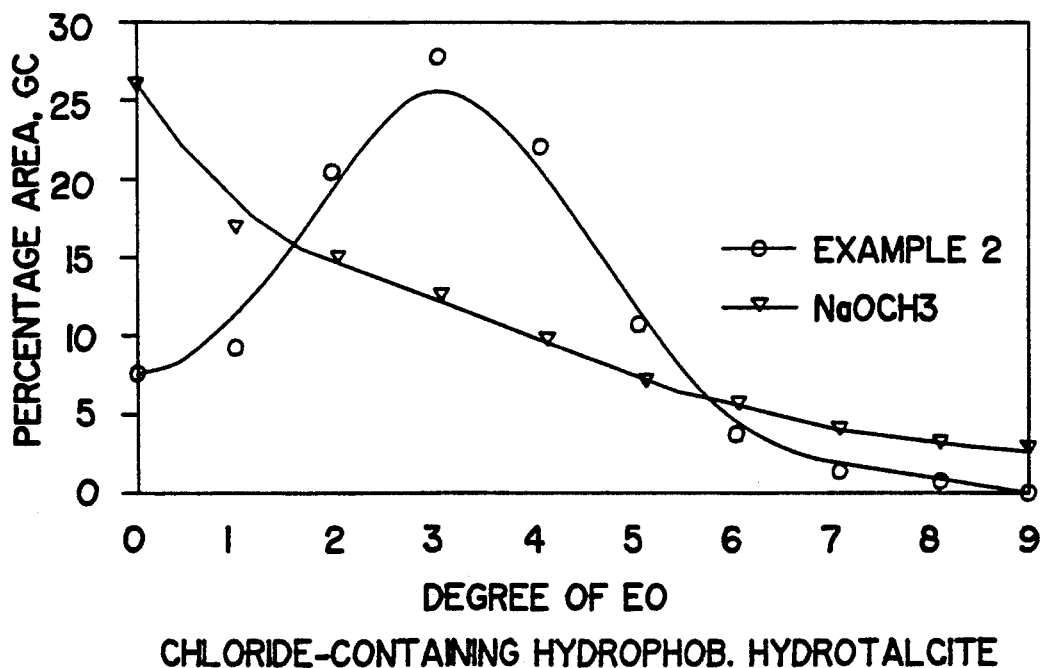
Figure 3:
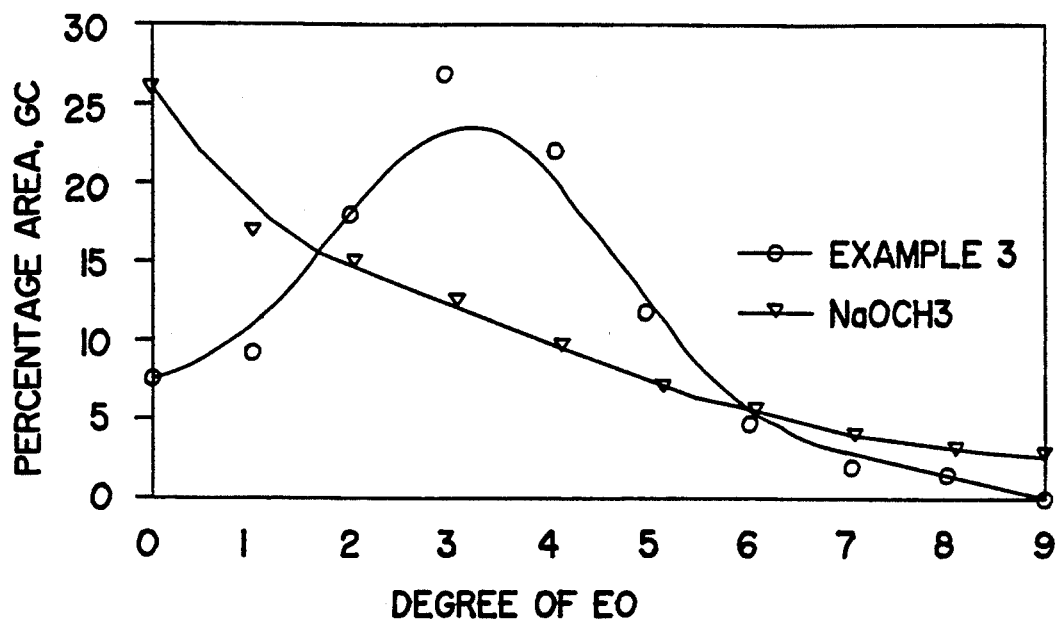
Figure 4:
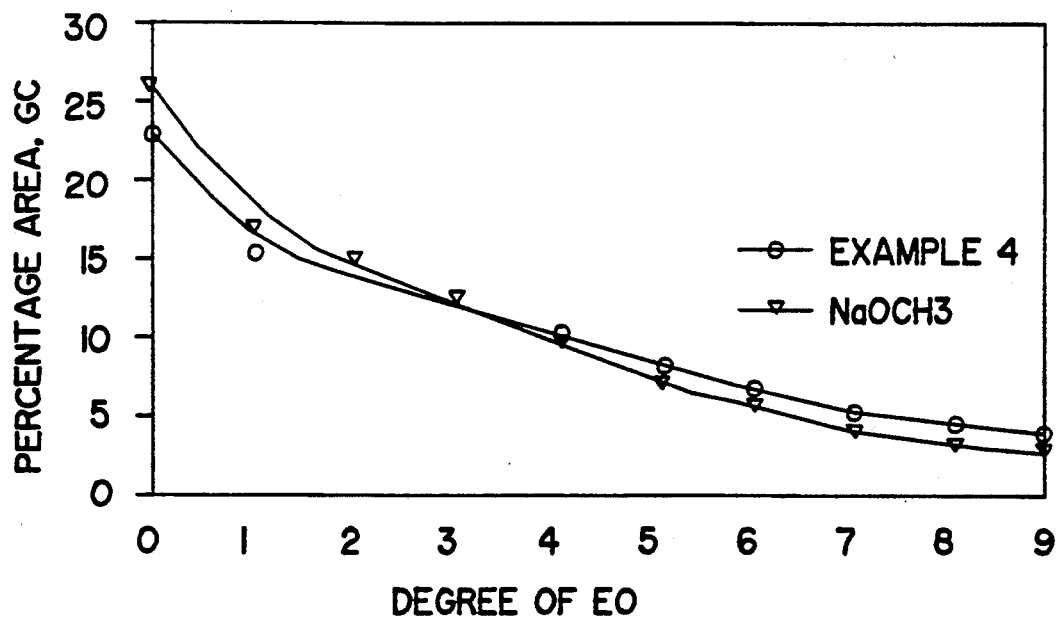
Figure 5:
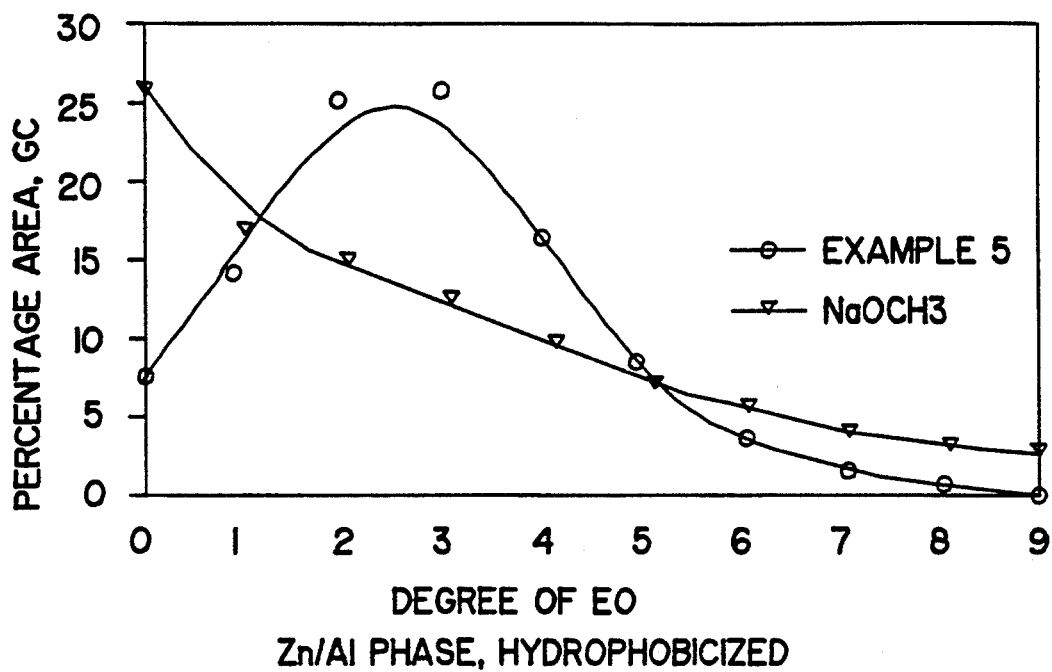
Figure 6:
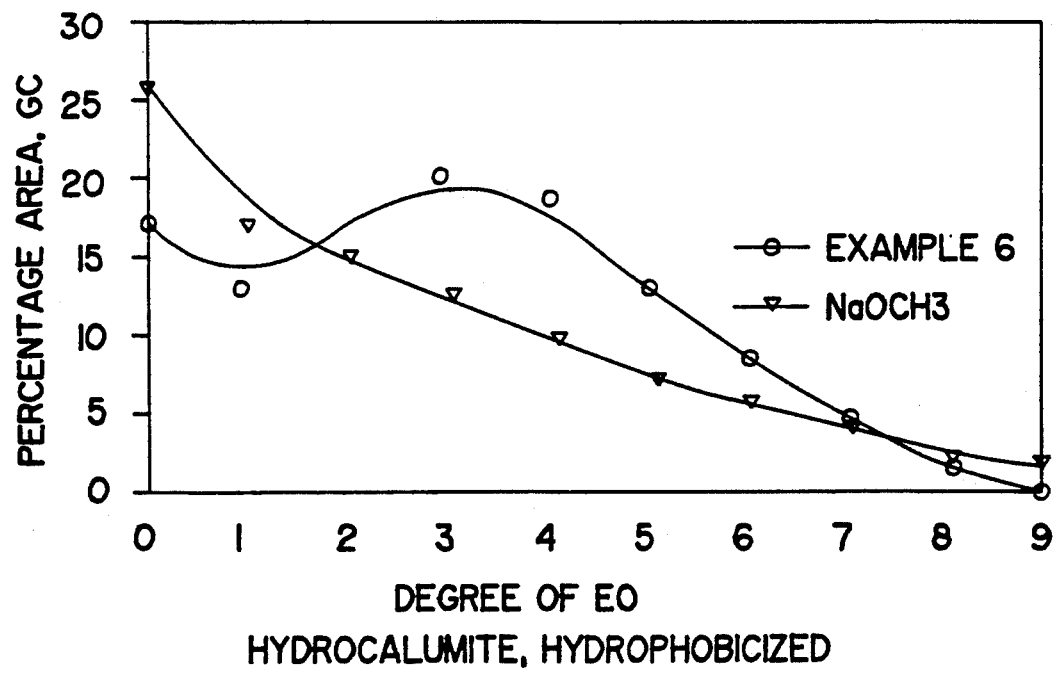

Accordingly, the present invention relates to hydrophobicized double layer hydroxide compounds corresponding to general formula (I)

$$(M(II)_{1-x}M(III)_x(OH)_2)A_a\ B_b * z\ H_2O \qquad (I)$$

in which M(II) is a divalent metal cation selected from the group consisting of magnesium, zinc, calcium, iron, cobalt, copper, cadmium, nickel and manganese, in which M(III) is a trivalent metal cation selected from the group consisting of aluminium, iron, chromium, manganese, bismuth and cerium, in which A is an equivalent of a monoanion of an aliphatic $C_{2\text{-}34}$ monocarboxylic acid or an equivalent of a dianion of an aliphatic $C_{4\text{-}44}$ dicarboxylic acid, in which B is an anion from the group consisting of carbonate, hydrogen carbonate, sulfate, nitrate, nitrite, phosphate, hydroxide and halides and in which the conditions $0.1 \leq x \leq 0.5$
$0 < a \leq 0.5$
$0 \leq b \leq 0.5$
$0 < a+b \leq 0.5$
$0 \leq z \leq 10$ apply, compounds containing the combinations of magnesium and aluminium with carbonate and/or sulfate being excluded.

The present invention also relates to a process for the production of hydrophobicized double layer hydroxide compounds corresponding to general formula (I), characterized in that double layer hydroxide compounds corresponding to general formula (II)

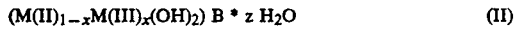

$$(M(II)_{1-x}M(III)_x(OH)_2) \text{ B } \cdot \text{ z } H_2O \qquad (II)$$

in which M(II), M(III), B, x and z are as defined above, excluding compounds containing the combinations of magnesium and aluminium with carbonate and/or sulfate, are reacted with at least one aliphatic $C_{2\text{-}34}$ monocarboxylic acid and/or at least one $C_{4\text{-}44}$ aliphatic dicarboxylic acid either a) in an organic solvent and the solvent is removed by drying at 20° to 150° C. or
b) are directly reacted with one another by stirring or kneading or
c) the double layer hydroxide compounds corresponding to general formula (II) are reacted with an alkali metal and/or alkaline earth metal salt of the mono- and/or dicarboxylic acids in aqueous suspension.

The anions A of the monocarboxylic acids, which may be used for the hydrophobicization of double layer hydroxide compounds, are for example those of the $C_{2\text{-}34}$ monocarboxylic acids, preferably $C_{6\text{-}22}$ fatty acids of natural or synthetic origin, more particularly linear, saturated or unsaturated fatty acids, including technical mixtures thereof, which are obtainable by hydrolysis from animal and/or vegetable fats and oils, for example from coconut oil, palm kernel oil, palm oil, soybean oil, sunflower oil, rapeseed oil, cottonseed oil, fish oil, beef tallow and lard.

Typical examples are caproic acid, caprylic acid, capric acid, lauric acid, myristic acid, palmitic acid, palmitoleic acid, stearic acid, oleic acid, elaidic acid, petroselic acid, linoleic acid, linolenic acid, arachic acid, gadoleic acid, behenic acid and erucic acid; also methyl-branched, saturated and unsaturated $C_{10\text{-}22}$ fatty acids which are formed as secondary products in the dimerization of the corresponding unsaturated fatty acids. However, $C_{2\text{-}5}$ monocarboxylic acids, such as preferably acetic acid or propionic acid, may also be used. Lauric acid and stearic acid are particularly preferred.

Typical examples of dicarboxylic acids A which are suitable for the hydrophobicization of double layer hydroxide compounds are succinic acid, maleic acid, fumaric acid, adipic acid, pimelic acid, suberic acid, sebacic acid and the like; also so-called dimer fatty acids which may be obtained, for example, from oleic acid or tall oil fatty acid and may contain up to 44 carbon atoms. The dimerization products of saturated, mono- and/or polyunsaturated $C_{16\text{-}22}$ monomer fatty acids, such as palmitoleic acid, oleic acid, gadoleic acid, erucic acid, ricinoleic acid, linoleic acid, linolenic acid, arachidonic acid and behenic acid, may also be used.

In one preferred embodiment of the present invention, the anions A of $C_{6\text{-}22}$ monocarboxylic acids or $C_{8\text{-}36}$ dicarboxylic acids, including dimer fatty acids, are used for hydrophobicizing the double layer hydroxide compounds.

According to the invention, the anions B are selected from the group consisting of carbonate, hydrogen carbonate, sulfate, nitrate, nitrite, phosphate, hydroxide and halides, depending on the origin of the double layer hydroxide compounds corresponding to general formula II.

According to the invention, the number ratio of a to b in the hydrophobicized double layer hydroxide compounds corresponding to general formula (I) should be in the range from 0.49:0.01 to 0.05:0.45 and, more particularly, in the range from 0.3:0.02 to 0.05:0.25. A high degree of exchange or hydrophobicization is required in the compounds corresponding to general formula (I) so that all monobasic or polybasic inorganic anions B in the compounds corresponding to general formula (I) are exchanged. According to the invention, complete hydrophobicization occurs in particular in cases where $a > x$ is achieved.

Accordingly, hydrophobicized double layer hydroxide compounds of general formula (I) which, based on their total weight, contain 15 to 70% by weight and more particularly 20 to 50% by weight of the anions A of $C_{6\text{-}22}$ monocarboxylic acids or 10 to 60% by weight and more particularly 15 to 50% by weight of the dianions A of the $C_{8\text{-}36}$ dicarboxylic acids are also preferred.

The hydrophobicized double layer hydroxide compounds may be produced by various methods, for example by direct reaction of natural or synthetic double layer hydroxide compounds with mono- and/or dicarboxylic acids in a kneader or in the presence of organic solvents and by reaction of the double layer hydroxide compounds with an aqueous suspension of a mono- and/or dicarboxylic acid salt.

In a preferred embodiment of the present invention, the hydrophobicized double layer hydroxide compounds are prepared in a low-boiling organic solvent, preferably $C_{1\text{-}6}$ alcohols, open-chain and cyclic ethers and/or ketones, by reaction of monocarboxylic acids and/or dicarboxylic acids with the double layer hydroxide compounds corresponding to general formula (I). In a particularly preferred embodiment, hydrophobicization is carried out in isopropanol, diethyl ether, tetrahydrofuran and/or acetone.

In another preferred embodiment, the molar ratio between the double layer hydroxide compound used and the monocarboxylic acid (or dicarboxylic acid) is 6:1 (3:1) to 1:10 (1:5) and preferably 3:1 (1.5:1) to 1:3 (1:1.5). As known to the expert, the molar ratio will have to be adjusted to those anions of the particular double layer hydroxide compounds used which are available during the exchange.

The process according to the invention may be carried out at temperatures of 20° to 120° C. and is preferably carried out at temperatures of 40° to 100° C., the double layer hydroxide compound and the carboxylic acid (or dicarboxylic acid) generally being heated under reflux in the particular organic solvent for 0.5 to 8 hours and preferably for 1 to 6 hours.

In another preferred embodiment of the present invention, the organic solvent is removed over a period of 0.5 to 3 hours and preferably over a period of 1 to 2 hours at temperatures in the range from 20° to 150° C. and preferably at temperatures in the range from 50° to 120° C.

In addition, the hydrophobicized double layer hydroxide compounds according to the invention may also be obtained by direct reaction of double layer hydroxide compounds with mono- and/or dicarboxylic acids in the absence of a solvent using a stirring unit of any kind, preferably a kneader.

In principle, the compounds of general formula (I) according to the invention may also be prepared analogously to the process known from DE 37 31 919 A1 by reaction of double layer hydroxide compounds with an aqueous suspension of an alkali metal salt and/or alkaline earth metal salt, preferably sodium salts of a mono- and/or dicarboxylic acid.

Finally, the hydrophobicized double layer hydroxide compounds may also be obtained from calcined double layer hydroxide compounds by reaction thereof with the mono- or dicarboxylic acids. Carbonate-free or carbonate-containing products may be obtained in the absence of air or $CO_2$ or in the presence of carbon dioxide.

It can be shown with the aid of X-ray diffractograms that the layer structure in the hydrophobicized double layer hydroxide compounds has remained intact with widening of the layer intervals.

The stoichiometric water content of the hydrophobicized double layer hydroxide compounds can be in the range from 0 to 10 molecules, depending on the method of production and the drying conditions. A range of 0 to 4 molecules is preferred and is generally established when the hydrophobicized double layer hydroxide compounds are dried to constant weight at temperatures of 100° to 250° C. and preferably at temperatures of 150° to 220° C., so that particularly high catalytic activity can be guaranteed.

The present invention also relates to the use of hydrophobicized double layer hydroxide compounds corresponding to general formula (I), excluding compounds containing combinations of magnesium and aluminium with carbonate, as alkoxylation catalysts for compounds containing active H atoms or for fatty acid esters.

The present invention is based in this regard on the observation that hydrophobicized double layer hydroxide compounds are suitable for the ethoxylation and propoxylation of compounds containing active H atoms and fatty acid esters. This observation is surprising because untreated natural or synthetic double layer hydroxide compounds, i.e. those in non-calcined form, and also a number of calcined compounds are not active as ethoxylation or propoxylation catalysts.

In the context of the invention, compounds containing active H atoms are, for example, fatty alcohols, fatty acids and amines which are formed in the ethoxylation or propoxylation of nonionic detergents. A typical example of this is the reaction of fatty alcohols typically containing 10 to 18 carbon atoms with ethylene oxide and/or propylene oxide in the presence of catalysts, the fatty alcohols reacting with several molecules of ethylene oxide and/or propylene oxide.

The following compounds inter alia have been used as catalysts for the above-mentioned polyalkoxylation:
calcium and strontium hydroxides, alkoxides and phenoxides (EP 0 092 256 A1),
calcium alkoxides (EP 0 091 146 A1).
barium hydroxide (EP 0 115 083 B1),
basic magnesium compounds, for example alkoxides (EP 0 082 569 A1),
magnesium and calcium fatty acid salts (EP 0 085 167 A1).

The catalysts mentioned above are attended inter alia by the disadvantage that they cannot readily be incorporated in the reaction system and/or are difficult to produce. Other typical alkoxylation catalysts are potassium hydroxide and sodium methylate.

A narrow range of the degree of polyalkoxylation is of particular importance for fatty alcohol polyalkoxylates (JAOCS, 63, 691 (1986), MAPPI, 52 (1986)). Accordingly, the so-called "narrow-range" alkoxylates have in particular the following advantages:
low flow points
relatively high smoke points
fewer mols alkoxide required to achieve solubility in water
less hydrotropes for introduction into liquid universal detergents
a relatively faint odor attributable to the presence of free (unreacted) fatty alcohols
reduction of pluming during the spray drying of detergent slurries containing fatty alcohol polyalkoxylate surfactants.

Using hydrophobicized double layer hydroxide compounds as catalysts in accordance with the invention, compounds containing active H atoms and fatty acid esters can be polyalkoxylated with high yields in short reaction times. The reaction products have a narrow range or homolog distribution, the distribution curve coming very close to the curve calculated in accordance with Poisson. The hydrophobicized double layer hydroxide compounds used in accordance with the invention have the advantage that they can readily be incorporated in the alkoxylation reaction mixture and can be removed again by simple measures by virtue of their insolubility in the reaction mixture. However, they may also remain in the reaction mixture providing their presence is not problematical in subsequent applications of the reaction products.

Examples of compounds which can be alkoxylated in accordance with the invention using hydrophobicized double layer hydroxide compounds are listed in the following:

$C_{6-22}$ fatty acids of natural or synthetic origin, more particularly linear, saturated or unsaturated fatty acids, including technical mixtures thereof, which can be obtained by hydrolysis from animal and/or vegetable fats and oils, for example from coconut oil, palm kernel oil, palm oil, soybean oil, sunflower oil, rapeseed oil, cottonseed oil, fish oil, beef tallow and lard. Typical examples are caproic acid, caprylic acid, capric acid, lauric acid, myristic acid, palmitic acid, palmitoleic acid, stearic acid, oleic acid, elaidic acid, petroselic acid, linoleic acid, linolenic acid, arachic acid, gadoleic acid, behenic acid, erucic acid, arachidonic acid and clupanodonic acid; also methyl-branched, saturated and unsaturated $C_{10-22}$ fatty acids, which are formed as secondary products in the dimerization of the corresponding unsaturated fatty acids, and $C_{1-7}$ monocarboxylic acids.

Hydroxyfatty acids of natural or synthetic origin, more particularly containing 16 to 22 carbon atoms, for example ricinoleic acid or 12-hydroxystearic acid.

Fatty acid amides. Derivatives of the above-mentioned linear, saturated or unsaturated fatty acids with ammonia or primary aliphatic amines containing 1 to 4 carbon atoms in the aliphatic substituent.

Alkanols. Saturated or unsaturated monoalkanols, more particularly hydrogenation products of the above-mentioned linear, saturated or unsaturated fatty acids or derivatives thereof, such as methyl esters, or glycerides; aliphatic or cyclic alkanols containing 2 to 6 carbon atoms, for example ethanol, propanol, butanol, hexanol and cyclohexanol; including the Guerbet alcohols derived from the above-mentioned monoalkanols.

Alkyl phenols. Mono-, di- or trialkyl phenols, more particularly containing 4 to 12 carbon atoms in the alkyl groups.

Polyglycols. Polyethylene or polypropylene glycols (average degree of polymerization 2 to 2000).

Fatty amines. More particularly primary fatty amines obtainable from nitriles of the above-mentioned linear, saturated or unsaturated fatty acids or the corresponding fatty alcohols; also mono- and dialkyl amines containing $C_{1-6}$ alkyl groups.

Fatty acid alkanolamides. Derivatives of the above-mentioned linear, saturated or unsaturated fatty acids with mono- or dialkanolamines, more particularly mono- or diethanolamine.

Vicinally hydroxy- or alkoxy-substituted alkanes. Ring opening products of 1,2-epoxyalkane mixtures containing 12 to 22 carbon atoms in the chain with polyfunctional alkanols containing 2 to 12 carbon atoms and 2 to 6 hydroxyl groups; but only if they are reacted with ethylene oxide or first with ethylene oxide and then with propylene oxide.

Fatty acid esters formed from the optionally methyl-branched fatty acids or monocarboxylic acids and hydroxyfatty fatty acids listed above and the alkanols listed above; also esters of these acids with polyols, for example with ethylene glycol, 1,2-propylene glycol, 1,2-butylene glycol, neopentyl glycol, glycerol, diglycerol, triglycerol, tetraglycerol, trimethylol propane, di-trimethylol propane, pentaerythritol, dipentaerythritol, and sugar alcohols, more particularly sorbitan.

As mentioned at the beginning, esters of the above-mentioned fatty acids with the above-mentioned polyols may also be present as partial esters or as technical ester mixtures containing partial esters, more particularly in the form of glycerides.

Preferred fatty acid esters for the ethoxylation and/or propoxylation according to the invention are formed from saturated or unsaturated, optionally methylbranched or optionally hydroxy-substituted $C_{8-22}$ fatty acids with $C_{1-4}$ alkanols or with glycerol.

The structure of the ethoxylated or propoxylated fatty acid esters obtained in accordance with the invention cannot always be clearly determined. Whereas esters of fatty acids and monoalkanols or full esters thereof would appear to react with polyols with insertion of ethyleneoxy and/or propyleneoxy units into the ester bond, it is not possible to determine the reaction products to which the reaction of ethylene oxide and/or propylene oxide with partial esters of fatty acids and polyols or of hydroxysubstituted fatty acids and monoalkanols leads; in this case, reactions could also take place at the free OH groups, particularly at free primary OH groups.

The derivatives to be produced in accordance with the invention using hydrophobicized double layer hydroxide compounds are commercially available products so that they need not be described in any more detail. They are all obtained by ethoxylation and/or propoxylation of starting compounds containing active hydrogen atoms or of fatty acid esters. Typical representatives are, for example, an addition product of 9 mol ethylene oxide with coconut oil fatty acid, an addition product of 2 mol ethylene oxide with a $C_{12-14}$ fatty alcohol mixture, an addition product of 3 mol ethylene oxide and S mol propylene oxide with a $C_{12-18}$ fatty alcohol mixture, an addition product of 10 mol ethylene oxide with nonyl phenol, an addition product of 7.3 tool ethylene oxide with glycerol, an addition product of 10 mol ethylene oxide with a diol mixture obtained by reaction of a $C_{12-16}$ 1,2-epoxyalkane mixture with ethylene glycol, an addition product of 12 mol ethylene oxide with a $C_{10-18}$ fatty amine mixture and an addition product of 4 mol ethylene oxide with coconut oil fatty acid monoethanolamide; also addition products of 41 mol ethylene oxide with castor oil, addition products of 25 mol ethylene oxide with hydrogenated castor oil, addition products of 7 parts by weight ethylene oxide with 10 parts by weight of a palmitic acid/stearic acid mono-/diglyceride mixture containing 40 to 45% by weight monoglyceride and addition products of 20 mol ethylene oxide with sorbitan monostearate.

In a preferred embodiment of the invention, the compounds containing active H atoms ethoxylatable or propoxylatable using the hydrophobicized double layer hydroxide compounds are selected from the group consisting of fatty acids, hydroxyfatty acids, fatty acid amides, alkanols, alkyl phenols, polyglycols, fatty amines, fatty acid alkanolamides or vicinally hydroxy- or alkoxy-substituted alkanes.

In another preferred embodiment, the hydrophobicized double layer hydroxide compounds are used in a quantity of 0.1 to 3% by weight and preferably in a quantity of 0.5 to 2% by weight, based on the end product of the ethoxylation or propoxylation reaction.

In another preferred embodiment of the invention, the reaction between compounds containing active hydrogen atoms or fatty acid esters on the one hand and ethylene and/or propylene oxide on the other hand is carried out in the presence of the hydrophobicized double layer hydroxide compounds according to the invention at a temperature of 125° to 180° C. and preferably 150° to 160° C. and under a pressure of 1 to 5 bar. The time required is determined by the desired degree of alkoxylation and is normally between 0.5 and 5 hours.

The following Examples are intended to illustrate the invention without limiting it in any way.

EXAMPLES

Example 1

Reaction of magaldrate with sodium laurate. 20 g magaldrate (commercial product of Giulini, Ludwigshafen, Germany) having the ideal formula $(Mg_{10}Al_5(OH)_{31})(SO_4)_2 * z\ H_2O$ were suspended in 200 ml water and, after the addition of a solution of 7.6 g sodium laurate in 70 ml water, the resulting suspension was stirred for 15 hours at 70° C. After filtration and washing, the white precipitate was dried at 200° C./100 mbar.

| Yield: | 20.2 g hydrophobicized magaldrate |
|---|---|
| Analyses: | 17.7% by weight Mg |
| | 9.5% by weight Al |
| | 18.7% by weight C |
| | 1.8% by weight SO$_4$ |
| Mg/Al ratio: | 2.1 |
| Al/laurate ratio: | 2.71 |

25.9% by weight laurate, x=0.33; a=0.14; b=0.04

Example 2

Reaction of chloride-containing hydrotalcite with sodium laurate. 20 g chloride-containing hydrotalcite (Mg$_6$Al$_2$(OH)$_{16}$)Cl$_2$ * 4 H$_2$O were suspended in 200 ml water and, after the addition of a solution of 15 g sodium laurate in 100 ml water, the resulting suspension was stirred for 3 hours at 70° C. After filtration and washing, the precipitate was dried at 105° C./100mbar. As a catalyst, the product was redtied at 200° C./100 mbar.

| Yield: | 26.3 g hydrophobicized hydrotalcite |
|---|---|
| Analyses: | 12.7% by weight Mg |
| | 7.6% by weight Al |
| | 25.7% by weight C |
| | 0.5% by weight Cl |
| Mg/Al ratio: | 1.9 |
| Al/laurate ratio: | 1.58 |

35.5% by weight laurate, x=0.35; a=0.22; b=0.02

Example 3

Reaction of nitrate-containing hydrotalcite with sodium laurate. 20 g of a dried nitrate-containing hydrotalcite having the ideal formula (Mg$_6$Al$_2$(OH)$_{16}$)(NO$_3$)$_2$ * n H$_2$O, prepared by precipitation of a magnesium and aluminium nitrate solution with excess ammonia, were suspended in 200 ml water and, after the addition of a solution of 13.4 g sodium laurate in 100 ml water, the resulting suspension was stirred overnight at 70° C. After filtration and washing, the precipitate was dried at 105° C./100 mbar.

| Yield: | 27.4 g hydrophobicized hydrotalcite |
|---|---|
| Analyses: | 17.3% by weight Mg |
| | 6.9% by weight Al |
| | 27.1% by weight C |
| | 6.8% by weight H |
| | 3.0% by weight NO$_3$— |
| Mg/Al ratio: | 2.78 |
| Al/laurate ratio: | 1.36 |

37.5% by weight laurate, x=0.26; a=0.19; b=0.05

Example 4

Reaction of pyroaurite with lauric acid. 10 g of a synthetic pyroaurite having the ideal formula (Mg$_6$Fe$_2$(OH)$_{16}$)CO$_3$ * 4.5 H$_2$O, were suspended in 150 ml isopropanol and 6.05 g lauric acid in 50 ml isopropanol were added to the resulting suspension at room temperature. The suspension was then heated to the reflux temperature and kept at that temperature for 5 h. After filtration and washing with isopropanol, the product was dried at 105° C./100 mbar.

| Yield: | 13.5 g hydrophobicized pyroaurite |
|---|---|
| Analyses: | 16.8% by weight Mg |
| | 12.7% by weight Fe |
| | 34.9% by weight C |
| | 6.8% by weight H |
| | <0.1% by weight CO$_3{}^{2-}$ |
| Mg/Fe ratio: | 3.04 |
| Fe/laurate ratio: | 0.94 |

48.3% by weight laurate, x=0.25; a=0.26

Example 5

Reaction of the Zn/Al 1 phase with lauric acid. The Zn/Al phase having the ideal formula (Zn$_{1-x}$Al$_x$(OH)$_2$)(CO$_3$)$_{x/2}$ * n H$_2$O with x=0.17 was synthesized by reaction of zinc oxide with an aqueous aluminium nitrate solution containing sodium carbonate. After filtration and washing, the product was dried. 40 g of this phase were reacted with 18.8 g lauric acid in 300 ml isopropanol below the reflux temperature. After filtration and washing with isopropanol, the product was dried at 105° C./100 mbar.

| Yield: | 51.9 g hydrophobicized Zn/Al phase |
|---|---|
| Analyses: | 39.1% by weight Zn |
| | 3.3% by weight Al |
| | 30.4% by weight C |
| | 5.8% by weight H |
| | <0.1% by weight CO$_3{}^{2-}$ |
| Zn/Al ratio: | 4.89 |
| Al/laurate ratio: | 0.58 |

42% by weight laurate, x=0.17; a=0.29

Example 6

Reaction of hydrocalumite with lauric acid. Hydrocalumite having the ideal formula (Ca$_2$Al(OH)$_6$)NO$_3$ * n H$_2$O was synthesized by reaction of calcium and aluminium nitrate in alkaline solution in the absence of air. After filtration and washing, 20 g of the dried product were reacted with 12.2 g lauric acid in 300 ml water for 5 h at 70° C., washed and dried at 110° C./100 mbar.

| Yield: | 27.3 g hydrophobicized hydrocalumite |
|---|---|
| Analyses: | 30.5% by weight Ca |
| | 9.7% by weight Al |
| | 34.5% by weight C |
| | 7.2% by weight H |
| Ca/Al ratio: | 2.12 |
| Al/laurate ratio: | 1.50 |

47.7% by weight laurate, x=0.32; a=0.21

Example 7

Preparation of a Zn/Al phase and reaction with lauric acid. A solution of 178.5 g zinc nitrate (0.6 mol) and 75.0 g aluminium nitrate (0.2 mol) was added to an alkaline sodium carbonate solution so that the pH value was always above 9. After the addition, the solution was heated for 5 hours to 70° C., filtered and washed. The colorless product was dried to constant weight at 110° C.

| Yield: | 70 g colorless powder |
|---|---|
| Analyses: | 33.5% by weight Zn |
| | 16.5% by weight Al (x = 0.5) |

10 g of the powder were reacted under reflux with 1.25 g lauric acid for 5 h at 70° C. in 200 ml tetrahydrofuran, filtered, washed and dried at 110° C./100 mbar.

| Yield:            | 10.9 g partly hydrophobicized Zn/Al phase |
|---|---|
| Analyses:         | 30.5% by weight Zn |
|                   | 15.3% by weight Al |
|                   | 7.0% by weight C |
|                   | 8.0% by weight $CO_3^{2-}$ |
| Al/laurate ratio: | 11.76 |

9.61% by weight laurate, $x=0.5$; $a=0.05$; $b=0.24$

Example 8

Example 3 was repeated using 8.2 g sodium caproate.

| Yield:             | 24.6 g hydrophobicized hydrotalcite |
|---|---|
| Analyses:          | 22.5% by weight Mg |
|                    | 7.0% by weight Al |
|                    | 5.1% by weight C |
|                    | 8.5% by weight $NO_3-$ |
| Al/caproate ratio: | 3.66 |

8.17% by weight caproate, $x=0.22$; $a=0.08$; $b=0.12$

Example 9

Example 3 was repeated using 18.4 g sodium stearate.

| Yield:             | 35.4 g hydrophobicized hydrotalcite |
|---|---|
| Analyses:          | 12.9% by weight Mg |
|                    | 4.0% by weight Al |
|                    | 32.6% by weight C |
|                    | 4.7% by weight $NO_3-$ |
| Al/stearate ratio: | 0.98 |

42.85 by weight stearate, $x=0.22$; $a=0.22$; $b=0.10$

Example 10

Example 3 was repeated using 36.1 g the sodium salt of a $C_{36}$ dimer fatty acid.

| Yield:                 | 30.7 g hydrophobicized hydrotalcite |
|---|---|
| Analyses:              | 21.1% by weight Mg |
|                        | 6.5% by weight Al |
|                        | 11.1% by weight C |
|                        | 7.8% by weight $NO_3-$ |
| Al/dicarboxylate ratio:| 9.38 |

14.5% by weight dicarboxylate, $x=0.22$; $a=0.06$; $b=0.16$

Example 11

Reaction of a Zn/Al phase with stearic acid in a kneader. 60 g $(Zn_{1-x}Al_x(OH)_2)(CO_3)_{x/2}$ * z $H_2O$ with $x=0.24$ were reacted with 20.1 g stearic acid in a kneader for 3 h at 80° C. A colorless powder was obtained.

| Yield:             | 79.0 g hydrophobicized Zn/Al phase |
|---|---|
| Analyses:          | 38.6% by weight Zn |
|                    | 5.1% by weight Al |
|                    | 20.7% by weight C |
| Al/stearate ratio: | 1.97 |

27.1% by weight stearate, $x=0.24$; $a=0.13$

Example 12

Reaction of nitrate-containing hydrotalcite with stearic acid in a kneader. 40 g of the hydrotalcite phase $(Mg_{1-x}Al_x(OH)_2)(NO_3)_x$ * z $H_2O$ with $x=0.25$ were kneaded with 40 ml isopropanol to a paste-like consistency and 8.5 g stearic acid were added to the resulting paste. After addition of 5 ml concentrated ammonia (25%), the kneader was heated to 80° C. and kneaded to dryness.

| Yield: | 47.0 g hydrophobicized hydrotalcite |
|---|---|

To decompose the ammonium nitrate, the product was carefully dried at 200° C.

| Analyses:          | 18.3% by weight Mg |
|---|---|
|                    | 6.9% by weight Al |
|                    | 15.5% by weight C |
|                    | 7.0% by weight $NO_3-$ |
| Al/stearate ratio: | 3.57 |

20.3% by weight stearate, $x=0.25$; $a=0.07$; $b=0.11$

Example 13

Preparation of an Mg/Bi phase and reaction with laurie acid. A solution of 237 g bismuth nitrate (0.6 mol) in dilute nitric acid was combined and stirred with a solution of 461.5 g magnesium nitrate (1.8 mol). The resulting mixture was added with intensive stirring to an alkaline sodium carbonate solution which was always present in excess. A yellow precipitate was formed, becoming colorless during the reaction. To complete the reaction, the suspension was heated to 80° C. After cooling, the suspension was filtered, washed and dried. 285 g of a colorless powder were obtained.

| Analyses: | 10.0% by weight Mg |
|---|---|
|           | 56.0% by weight Bi, $x = 0.39$ |

135 g of the powder were suspended in 400 ml isopropanol and a solution of 56.1 g lauric acid in 200 ml isopropanol were added to the resulting suspension. The suspension obtained was heated for 5 h to the reflux temperature and subsequently filtered, washed and dried.

| Yield:            | 180 g hydrophobicized Mg/Bi phase |
|---|---|
| Analyses:         | 7.4% by weight Mg |
|                   | 47.2% by weight Bi |
|                   | 23.2% by weight C |
| Bi/laurate ratio: | 1.40 |

32.1% by weight laurate, $x=0.43$; $a=0.30$

General procedure for the production of alkoxylates of compounds containing active H atoms using the catalysts according to the invention The compound to be alkoxylated was introduced into a stirred pressure reactor and the catalysts produced in accordance with Examples 1 to 8, which had been pre-dried at 200° C./100 mbar, were added. The reactor was purged with nitrogen and evacuated for 30 minutes at a temperature of 100° C. The temperature was then increased to approx. 150°-160° C. and ethylene oxide or propylene oxide was introduced under a maximum pressure of 4 to 5 bar. The temperature of the exothermic reaction should not exceed 180° C. On completion of the reaction, the reaction mixture was left to react for 30 minutes after which the reactor was evacuated for another 30 minutes at 120° C. The desired reaction product was obtained after cooling and removal of the heterogeneous catalyst by filtration.

Using a commercially available $C_{12/14}$ fatty alcohol cut (Lorol ® Spezial, hydroxyl value 280, a product of Henkel KGaA, batch size 300 g fatty alcohol), a fatty alcohol ethoxylate was prepared in accordance with the above procedure by addition of 3 mol ethylene oxide per mol fatty alcohol.

The particular catalysts used, the concentration used, the reaction time and the hydroxyl values of the reaction products are listed in Table 1 below. In addition, the corresponding product distributions obtained by GC analysis are shown in the accompanying Figures of Examples 1 to 6.

TABLE 1

| Catalyst | c (Cat) % by weight | t h | OHV | HLD | FIG. |
|---|---|---|---|---|---|
| Ex. 1 | 0.5 | 0.75 | 174 | Good | 1 |
| Ex. 2 | 0.5 | 1 | 170 | Good | 2 |
| Ex. 3 | 0.5 | 0.8 | 173 | Good | 3 |
| Ex. 4 | 0.5 | 2.75 | 176 | Moderate | 4 |
| Ex. 5 | 0.5 | 3.5 | 178 | Good | 5 |
| Ex. 6 | 0.5 | 2.3 | 178 | Moderate | 6 |

Legend: c (Cat) = catalyst concentration
t = reaction time
OHV = hydroxyl value
HLD = homolog distribution

We claim:

1. A hydrophobicized double layer hydroxide compound of the formula $$(M(II)_{1-x}M(III)_x(OH)_2)A_a B_b \cdot z H_2O \quad (I)$$

wherein M(II) is a divalent metal cation selected from the group consisting of magnesium, zinc, calcium, iron, cobalt, copper, cadmium, nickel and manganese;
M(III) is a trivalent metal cation selected from the group consisting of aluminum, iron, chromium, manganese, bismuth and cerium;
A is an equivalent of a monoanion of an aliphatic $C_{2-34}$ monocarboxylic acid or an equivalent of a dianion of an aliphatic $C_{4-44}$ dicarboxylic acid;
B is an anion selected from the group consisting of carbonate, hydrogen carbonate, sulfate, nitrate, nitrite, phosphate, hydroxide, and halide;
$0.1 \leq x \leq 0.5$;
$0 < a \leq 0.5$;
$0 \leq b \leq 0.5$;
$0 < a+b \leq 0.5$; and
$0 \leq z \leq 10$;
and wherein the number ratio of a to b is in the range of from 0.49:0.01 to 0.05:0.45; provided that the compound of formula I does not include compounds that contain both magnesium and aluminum as cations and either or both of carbonate and sulfate as anions.

2. The compound of claim 1, wherein the number ratio of a to b is from 0.3:0.02 to 0.05:0.25.

3. A compound of claim 1 wherein A is a monoanion of at least one $C_{6-22}$ monocarboxylic acid.

4. A compound of claim 3 wherein from 15 to 70% by weight of said monoanion is present, based on the total weight of the compound.

5. A compound of claim 4 wherein from 20 to 50% by weight of said monoanion is present therein.

6. A compound of claim 1 wherein anion A is a dianion derived from at least one $C_{8-36}$ dicarboxylic acid.

7. A compound of claim 6 wherein the dianion is derived from a dimer fatty acid.

8. A compound of claim 6 wherein from 10 to 60% by weight of dianion is present, based on the total weight of the compound.

9. A compound of claim 8 wherein from 15 to 50% by weight of a dianion is present therein.

10. A compound of claim 1 wherein the number ratio of a to b is in the range of from 0.49:0.01 to 0.05:0.45; A is either a monoanion of at least one $C_{6-22}$ monocarboxylic acid present in from 15 to 70% by weight or is a dianion derived from at least one $C_{8-36}$ dicarboxylic acid present in from 10 to 60% by weight; wherein the above percentages by weight are based on the total weight of the compound.

11. A compound of claim 10 wherein the monoanion when present is present in from 20 to 50% by weight and the dianion when present is present in from 15 to 50% by weight.

12. A process for the preparation of a hydrophobicized double layer hydroxide compound of the formula $$(M(II)_{1-x}M(III)_x(OH)_2)A_a B_b \cdot z H_2O \quad (I)$$

wherein M(II) is a divalent metal cation selected from the group consisting of magnesium, zinc, calcium, iron, cobalt, copper, cadmium, nickel and manganese;
M(III) is a trivalent metal cation selected from the group consisting of aluminum, iron, chromium, manganese, bismuth and cerium;
A is an equivalent of a monoanion of an aliphatic $C_{2-34}$ monocarboxylic acid or an equivalent of a dianion of an aliphatic $C_{4-44}$ dicarboxylic acid;
B is an anion selected from the group consisting of carbonate, hydrogen carbonate, sulfate, nitrate, nitrite, phosphate, hydroxide, and halide;
$0.1 \leq x \leq 0.5$;
$0 < a \leq 0.5$;
$0 \leq b \leq 0.5$;
$0 < a+b \leq 0.5$; and
$0 \leq z \leq 10$;
provided that the compound of formula I does not include compounds that contain both magnesium and aluminum as cations and either or both of carbonate and sulfate as anions, comprising reacting at least one double-layer hydroxide compound of the formula $$(M(II)_{1-x}M(III)_x(OH)_2) B \cdot z H_2O \quad (II)$$

in which M(II), M(III), B, x and z are as defined above, but excluding compounds of formula II that contain both magnesium and aluminum as cations and either or both of carbonate and sulfate as anions, with at least one aliphatic $C_{2-34}$ monocarboxylic acid and/or at least one $C_{4-44}$ aliphatic dicarboxylic acid by either
a) carrying out the reaction in an organic solvent, and removing the solvent thereafter by drying at 20° to 150° C., or
b) directly reacting the above components together, or
c) reacting the at least one double layer hydroxide compound of formula (II) with an alkali metal and/or alkaline earth metal salt of the at least one mono- and/or dicarboxylic acid in aqueous suspension.

13. The process of claim 12 wherein the organic solvent is selected from the group consisting of a $C_{1-6}$ alcohol, an open-chain ether, a cyclic ether, and a ketone.

14. The process of claim 12 wherein the molar ratio of the compound of formula II to the aliphatic acid is from 6:1 to 1:10 when the acid is monocarboxylic, and from 3:1 to 1:5 when the acid is dicarboxylic, and the reaction temperature is from 20° to 120° C.

15. The process of claim 14 wherein the molar ratio is from 3:1 to 1:3 when the acid is monocarboxylic, and from 1.5:1 to 1:1.5 when the acid is dicarboxylic.

16. The process of claim 12 wherein when the reaction is carried out in an organic solvent, the solvent is removed by drying at a temperature of 40° to 100° C. for a period of from 0.5 to 3 hours.

17. In a process for the alkoxylation of a compound containing an active hydrogen atom or a fatty acid ester in the presence of an alkoxylation catalyst, the improvement wherein the catalyst is at least one compound of claim 1.

18. The process of claim 17 wherein the alkoxylation is of a compound containing an active hydrogen atom selected from the group consisting of fatty acids, hydroxy-fatty acids, fatty acid amides, alkanols, alkyl phenols, polyglycols, fatty amines, fatty acid alkanolamides, and vicinally hydroxy- or alkoxy-substituted alkanes.

19. The process of claim 17 wherein from 0.1 to 3% by weight of a compound of claim 1 is present, based on the end product of the alkoxylation reaction.

* * * * *